US010610735B2

(12) United States Patent
Harrison

(10) Patent No.: US 10,610,735 B2
(45) Date of Patent: Apr. 7, 2020

(54) ASSESSMENT OF PHYSICAL FITNESS OF AN ANIMAL OR HUMAN INDIVIDUAL

(71) Applicant: Curo Diagnostics ApS, Bagsvaerd (DK)

(72) Inventor: Adrian Paul Harrison, Frederiksberg C (DK)

(73) Assignee: Curo Diagnostics ApS, Bagsvaerd (DK)

( * ) Notice: Subject to any disclaimer, the term of this patent is extended or adjusted under 35 U.S.C. 154(b) by 143 days.

(21) Appl. No.: 15/534,579

(22) PCT Filed: Dec. 11, 2015

(86) PCT No.: PCT/EP2015/079433
§ 371 (c)(1),
(2) Date: Jun. 9, 2017

(87) PCT Pub. No.: WO2016/092077
PCT Pub. Date: Jun. 16, 2016

(65) Prior Publication Data
US 2017/0361160 A1 Dec. 21, 2017

(30) Foreign Application Priority Data
Dec. 11, 2014 (EP) .................................... 14197260

(51) Int. Cl.
*A63B 24/00* (2006.01)
*A61B 5/00* (2006.01)
(Continued)

(52) U.S. Cl.
CPC ...... *A63B 24/0062* (2013.01); *A61B 5/04012* (2013.01); *A61B 5/0488* (2013.01);
(Continued)

(58) Field of Classification Search
CPC .................. A61B 5/224; A61B 5/4519; A63B 2024/0065; A63B 2230/60; A63B 24/0062
See application file for complete search history.

(56) References Cited

U.S. PATENT DOCUMENTS 6,028,942 A 2/2000 Greenberger
2004/0082877 A1 4/2004 Kouou
(Continued)

FOREIGN PATENT DOCUMENTS

WO WO 2004/002191 A1 12/2003
WO WO 2007/071812 A1 6/2007
(Continued)

OTHER PUBLICATIONS

Barry, et al, Acoustic Myography: A Noninvasive Monitor of Motor Unit Fatigue, Muscle and Nerve, John Wiley & Sons, vol. 8, No. 3, Mar./Apr. 1985.
(Continued)

*Primary Examiner* — Christine H Matthews
(74) *Attorney, Agent, or Firm* — Woodard, Emhardt, Henry, Reeves & Wagner, LLP

(57) ABSTRACT

The invention determines an efficiency value (E) denoting preferably the relative period of muscle fiber activity during a recorded period of exercise, and a strength value (S) representing the number of muscle fibers recruited during a movement as part of the exercise or of a muscle contraction, and a temporal value (T) representing the frequency with which muscle fibers are activated repeatedly during exercise, and finally combines the efficiency value (E), the strength value (S) and the temporal value (T) by a linear combination to obtain an index value (ESTi) indicative of the fitness level of the individual. The obtained ESTi Score is useful for assessing the training level of an animal or human individual and the individual's potential for different
(Continued)

types of sports and other activity. Also the effect of past training or diet can be assessed, and the possible need for changes in training or diet can be assessed.

10 Claims, 2 Drawing Sheets

(51) Int. Cl.
| | | |
|---|---|---|
| *A61B 7/00* | (2006.01) | |
| *A61B 5/04* | (2006.01) | |
| *A61B 5/0488* | (2006.01) | |
| *A61B 5/22* | (2006.01) | |
| *G09B 19/00* | (2006.01) | |

(52) U.S. Cl.
CPC .............. *A61B 5/221* (2013.01); *A61B 5/224* (2013.01); *A61B 5/4519* (2013.01); *A61B 5/486* (2013.01); *A61B 5/72* (2013.01); *A61B 7/006* (2013.01); *G09B 19/0092* (2013.01); *A61B 5/0093* (2013.01); *A61B 5/22* (2013.01); *A63B 2024/0065* (2013.01); *A63B 2230/60* (2013.01)

(56) References Cited

U.S. PATENT DOCUMENTS

| | | |
|---|---|---|
| 2007/0232869 A1 | 10/2007 | Kanzaki |
| 2009/0170663 A1 | 7/2009 | Cox |
| 2010/0262042 A1 | 10/2010 | Kim |
| 2011/0196262 A1 | 8/2011 | McLeod |
| 2012/0108999 A1 | 5/2012 | Leininger |

FOREIGN PATENT DOCUMENTS

| | | |
|---|---|---|
| WO | WO 2007/112440 A2 | 10/2007 |
| WO | WO 2011/123071 A1 | 10/2011 |

OTHER PUBLICATIONS

Dalton, et al, Frequency of Acoustic Myography During Isometric Contraction of Fresh and Fatigued Muscle and During Dynamic Contractions, Muscle & Nerve, pp. 255-261, Mar. 1993.

Grundlehner, et al, Methods to Characterize Sensors for Capturing Body Sounds, 2011 Int. Conf. on Body Sensor Networks, 2011, Computer Society, pp. 59-64, May 23, 2011.

Harrison, et al, Portable acoustic myography—a realistic noninvasive method for assessment of muscle activity and coordination in human subjects in most home and sports settings; Physiological Reports, vol. 1, No. 2, Jul. 1, 2013.

Natini, Heart monitor and final result, Dat 301 Real Time, Feb. 21, 2013, retrieved from the Internet May 8, 2014.

Saumanahaii, Subdermal bone conduction headphones, Saumanahaii discussions, Jul. 1, 2013, retrived from the Internet.

Yijian, et al, The L-Z complexity of exercise-induced muscle fatigue based on acoustic myographe, Journal of Applied Physics, American Institute of Physics, vol. 115, No. 3, Jan. 15, 2014.

○     Selected muscle contractions, spikes above threshold
------    Threshold
CS     Cluster separaton

ASSESSMENT OF PHYSICAL FITNESS OF AN ANIMAL OR HUMAN INDIVIDUAL

FIELD OF THE INVENTION

The invention relates to assessment of physical fitness of an animal or human individual.

BACKGROUND OF THE INVENTION

For an athlete to achieve desired results it is necessary to know whether his or her food and training or other activities are optimal and lead to desired results. For the owner and potential buyers of e.g. a racehorse it is important to have objective methods of assessing the fitness of the horse and its potential, which ultimately influences its value.

Physical fitness of an animal or human individual can be assessed in different ways for different purposes and is often based on different measured physiological parameters such as dynamic and static muscle activity, heart rate, respiration, chemical analysis of body fluids etc.

It is desirable to have a method of assessing physical fitness of an animal or human individual that gives reliable and precise assessments, which can be used as a feedback during training enabling the individual and the individual's coach to determine the effect of training activities.

SUMMARY OF THE INVENTION

The invention enables the user to follow the components that comprise muscle performance during exercise. It also allows you to direct your training protocol in a way that matches your specific needs.

In practice, it is not sufficient to simply measure the number of fibres active (strength amplitude) and their temporal summation (frequency) but also the way in which the Central Nervous System (CNS) recruits and uses the active fibres in a muscle should be considered. By combining the timing aspect of muscle fibre contraction one can start to assess the synchrony with which the CNS recruits active fibres in a muscle and in so doing, more accurately determine the significance of both amplitude and frequency.

The method of the invention comprises the following steps:

obtaining an electrical signal representing muscle activity of the individual during physical exercise, and identifying in the signal a plurality of first periods where the signal repeatedly exceeds a threshold, and a plurality of second periods where the signal is consistently below the threshold, determining a representative interval of durations of the plurality of first periods, identifying, among the plurality of first periods, two or more individual first periods each of a duration shorter than the representative interval of durations and separated by a separation period, where the combined duration of the two or more individual first periods and the separation period is within the representative interval of durations, and for first periods having durations within the representative interval of durations and for identified two or more individual first periods performing the following steps:

obtaining an efficiency value (E) by combining, by a linear combination, the durations of the first time periods and the durations of the second time periods, obtaining a strength value (S) representing the number of muscle fibres recruited during a movement as part of the exercise or of a muscle contraction, obtaining a temporal value (T) representing the frequency with which muscle fibres are activated repeatedly during a movement as part of the exercise or of a muscle contraction, and combining, by a mathematical operation such as a linear combination, the efficiency value (E), the strength value (S) and the temporal value (T) to obtain an index value (ESTi) indicative of the fitness level of the individual.

The EST index (ESTi) or ESTi Score can then be sent (preferably electronically and online) to a trainer or a coach, an athlete, a medic or a patient and used to follow or guide their physical performance level and suggest immediate or long term changes in the training program. It provides a more accurate assessment of muscle performance than current scores. An ESTi Score derived from an AMG (myoacoustic) signal provides information regarding muscle contraction alone, as it does not include the neuromuscular junction as with electro-myography.

When e.g. a horse or an athlete is physically active they are using skeletal muscles with the aid of the central nervous system. Muscles are controlled from the motor cortex deep within the brain via the brain stem and spinal cord and motorneurons that run uninterrupted to the muscle fibres. Planning of muscle activity occurs in the thalamus whilst coordination and timing occurs in the cerebellum.

Since muscle contraction is not only about how many muscle fibres you activate and how fast you fire them, but also about the synchrony of individual muscle fibre or motor unit contractions and relaxations it is advantageous for an accurate assessment of muscle function and training level that all three aspects be incorporated into a final score.

In combining the amplitude, frequency and timing (synchrony) aspects into one unified or combined assessment or score the invention provides a more precise means of assessing individual muscle performance than previous forms of assessment. Not only do we find a linear relation between the "ESTi Score" determined by the method of the invention and the weight lifted by a muscle group (e.g. m. Vastus lateralis), we also identify individual differences in the ability to use muscles for weight lifting or fast explosive activities such as kicking a ball.

The ESTi Score determined by the invention is a very individual assessment in that it can be used or adjusted to assess the function of diverse muscle groups performing very different functions such as weight lifting, sprinting, endurance etc. It can also be adjusted to assess different forms of physical activity such as cycling, running, cross-country horse riding, rowing etc.

Finally, it can be used to assess the way in which individuals use their muscles for specific physical tasks or activities, identifying the efficiency of use, or the combination of muscle groups activated to achieve a set goal e.g. whether a runner uses the medial head of gastrocnemius before later activating the lateral head of this muscle later in a run as the medial head begins to fatigue.

The precise weighting of the E, S and T parameters will most likely vary from individual to individual and most certainly vary from muscle group to muscle group, as well as with different forms of physical exercise.

A low ESTi Score is seen as being optimal, a high score as being something relatively inefficient and energy consuming and also indicative of a low level of training.

A high ESTi Score could be the result of a high E, a high S, or a high T parameter as well as any combination of these three.

Using the ESTi Score, an individual can change or direct their training program in a very specific fashion to improve their physical performance knowing precisely which of the three parameters need to be improved e.g. a high T value would perhaps require more slow, repetitive training movements to improve muscle/fibre synchrony.

DETAILED DESCRIPTION OF THE INVENTION

The invention obtains electrical signals representing muscle activity of an animal or human individual during exercise. Muscle activity can be for one or more muscles or muscle fibres. Sensors or transducers receiving such signals can be placed on the skin of the individual and examples of such transducers are skin electrodes and electroacoustic transducers such as microphones and piezoelectric transducers which output an electrical signal in response to sound signals emanating from muscles within the body of the individual and received by the transducer. Sensors and transducers may also be placed on or in a muscle or other internal organ.

Sensed signals representing muscle activity include electrical signals and sound signals, obtained invasively or non-invasively.

Figure 1:
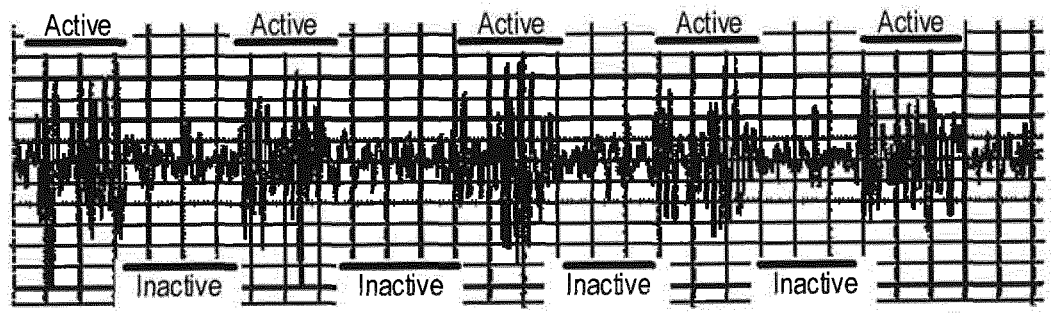
FIG. 1 shows a myoacoustic (AMG) signal measured on m. Gluteus medius of a horse in trot motion.

In FIG. 1 is shown a myoacoustic (AMG) signal measured on m. Gluteus medius of a horse in trot motion. The signal sequence shown has a duration of 3 ms and show periods with a high signal strength, i.e. above a threshold, marked "Active" and periods with a low signal strength, i.e. below the threshold, marked "Inactive".

Figure 2:
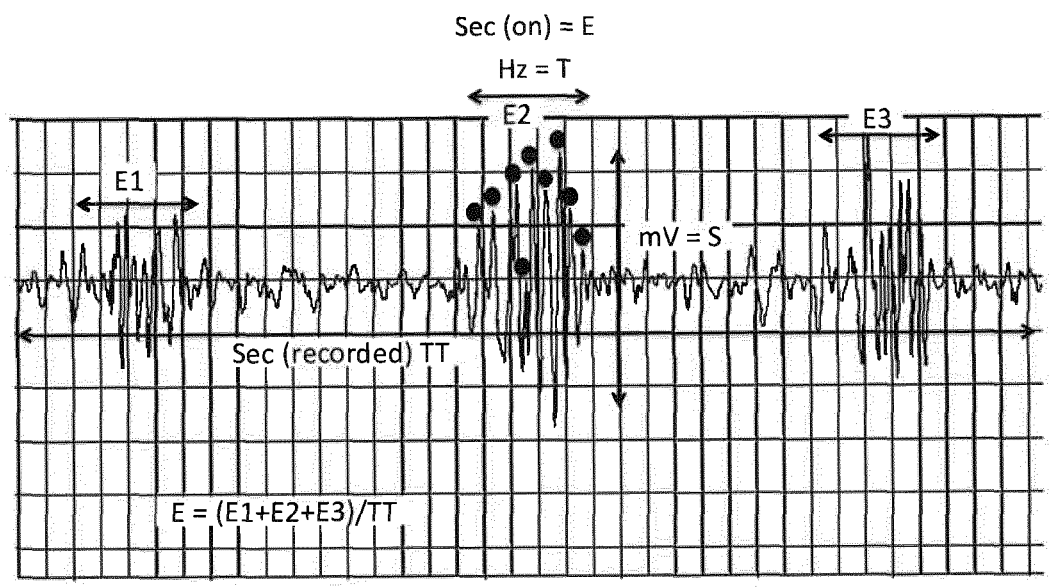
FIG. 2 shows an AMG signal with indications of how the E, S and T values can be determined.

FIG. 2 shows a similar signal on an expanded time scale. In active periods a value representing the signal amplitude is determined, and a value representing a "frequency" of the signal, e.g. an average frequency calculated as the number of peaks in the active period divided by the duration of the active period, is determined. Three active periods of respective durations E1, E2 and E3 are shown, and an example of calculating an efficiency value E is given where E is the equal to the duty cycle calculated as E=(E1+E2+E3)/TT where TT is the total time. Other mathematical calculations can be done, such as the ratio of the active time to the inactive time, where active time and inactive time can be individually weighted depending on the type of exercise, the muscle and the individual animal or human being.

A strength value S is calculated as a value representing an "amplitude" of the measured signal, such as an average of the peak values, or a maximum or a minimum value, an RMS value or other.

A temporal value T is preferably calculated as the number of peaks, preferably substantially equidistant peaks, or oscillations divided by the duration of the active period. The temporal value T is thus a characteristic frequency.

The E, S and T values are then combined to an EST index, an ESTi Score, by a suitable mathematical operation, where each of the E, S and T values can be given individual weights. The combining mathematical operation can be e.g. a linear combination such as a (weighted) sum ESTi Score=a*E+b*S+c*T, and one or more of the E, S and T values can be multiplied or raised to a power with an integer or a real number as the exponent. The weighting factors a, b and c depend on e.g. the type of physical activity or work performed, and on the human or animal individual (animal species, training level and history etc.), different muscle groups, The obtained ESTi Score is useful for assessing the training level of an animal or human individual and the individual's potential for different types of sports and other activity. Also the effect of past training or diet can be assessed, and the possible need for changes in training or diet can be assessed.

Figure 3:
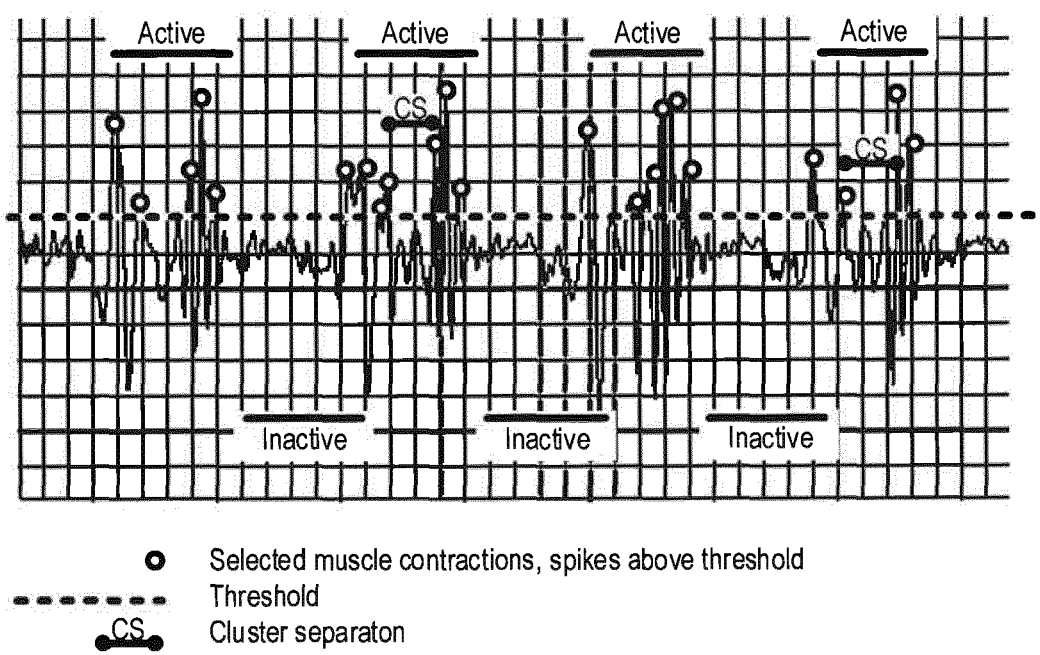
FIG. 3 shows an AMG signal where active periods contain clusters.

FIG. 3 shows an example of an AMG signal where, during active periods—that is to say periods of physical muscle activity/activities, one or more peaks do not exceed the threshold or are missing, whereby peaks above the threshold are not substantially equidistant as in FIGS. 1 and 2 but rather divided in clusters, in this example two clusters, separated by a cluster separation period CS. If clusters are treated as individual active periods, the resulting ESTi Score will be disturbed and become less significant and less reliable. It is therefore desirable to remove their influence on the ESTi Score, e.g. by equalising first periods containing clusters with "true" first periods e.g. as follows.

Clusters are distinguished from "true" or "significant" active periods, i.e. active periods without a cluster separation period CS, by having considerably shorter durations. Furthermore, a cluster separation period CS is longer than a predetermined number, e.g. one to three, of periods between spikes of the signal in true active periods, but shorter than the interval between true active periods. Such clusters may be considered and treated as being one true active period contributing to the calculation of the ESTi Score.

Also, two or more clusters including their intermediate cluster separation periods CS may be considered as being one active period if they have a combined duration including the cluster separation period CS, which differs by less than a predefined amount from the average of the true active periods, e.g. by one or two standard deviations. Such clusters, too, may be considered and treated as being one true active period contributing to the calculation of the ESTi Score.

Alternatively, detected clusters may be ignored and excluded from the calculation of the ESTi Score.

The invention claimed is:
1. A method of assessing a fitness level of an animal or human individual, the method comprising
    obtaining an electrical signal representing muscle activity of the animal or human individual during physical exercise, and identifying in the signal a plurality of first time periods where the signal repeatedly exceeds a threshold, and a plurality of second time periods where the signal is consistently below the threshold,
    determining a representative interval of durations of the plurality of first time periods,
    identifying, among the plurality of first time periods, two or more individual first time periods each of a duration shorter than the representative interval of durations and separated by a separation period, where a combined duration of the two or more individual first time periods and the separation period is within the representative interval of durations, and
    for first time periods having durations within the representative interval of durations and for identified two or more individual first time periods performing the following steps:

obtaining an efficiency value by combining, by a linear combination, the durations of the first time periods and durations of the second time periods, obtaining a strength value representing the number of muscle fibres recruited during a movement as part of the exercise or of a muscle contraction, obtaining a temporal value representing the frequency with which muscle fibres are activated repeatedly during a movement as part of the exercise or of a muscle contraction, and combining, by a mathematical operation, the efficiency value, the strength value and the temporal value to obtain an index value indicative of the fitness level of the animal or human individual.

2. The method of claim 1 wherein the signal representing muscle activity represents a sound signal generated in one or more muscles or muscle fibres.

3. The method of claim 1 wherein the signal representing muscle activity represents an electrical signal generated in one or more muscles or muscle fibres.

4. The method of claim 1 wherein the signal representing muscle activity is obtained non-invasively.

5. The method of claim 1 wherein the signal representing muscle activity is obtained invasively.

6. The method of claim 1 wherein one or more of the efficiency, strength and temporal values are multiplied or raised to a power with an integer or a fraction as the exponent.

7. Use of the index value obtained by a method according to claim 1 for assessing a training level of an animal or human individual and an animal or human individual's potential for different types of sports and other activity.

8. Use of the index value obtained by a method according to claim 1 for assessing an effect of past training or diet.

9. Use of the index value obtained by a method according to claim 1 for assessing a need for changes in training or diet.

10. The method of claim 1 wherein the mathematical operation is a linear combination.

* * * * *

UNITED STATES PATENT AND TRADEMARK OFFICE
CERTIFICATE OF CORRECTION

PATENT NO. : 10,610,735 B2  
APPLICATION NO. : 15/534579  
DATED : April 7, 2020  
INVENTOR(S) : Adrian Paul Harrison Page 1 of 1

It is certified that error appears in the above-identified patent and that said Letters Patent is hereby corrected as shown below:

On the Title Page

Item (71) Applicant city, replace "Bagsvaerd" with --Bagssværd--

Item (73) Assignee city, replace "Bagsvaerd" with --Bagssværd--

Signed and Sealed this  
Fourteenth Day of July, 2020

Andrei Iancu  
*Director of the United States Patent and Trademark Office*